United States Patent
Jeong et al.

(10) Patent No.: US 9,739,723 B1
(45) Date of Patent: Aug. 22, 2017

(54) METHODS OF DEFECT INSPECTION FOR PHOTOMASKS

(71) Applicant: SK hynix Inc., Gyeonggi-do (KR)

(72) Inventors: Goo Min Jeong, Chungcheongbuk-do (KR); Mun Sik Kim, Chungcheongbuk-do (KR)

(73) Assignee: SK Hynix Inc., Gyeonggi-do (KR)

( * ) Notice: Subject to any disclaimer, the term of this patent is extended or adjusted under 35 U.S.C. 154(b) by 0 days.

(21) Appl. No.: 15/191,209

(22) Filed: Jun. 23, 2016

(30) Foreign Application Priority Data

Feb. 22, 2016 (KR) .......................... 10-2016-0020499

(51) Int. Cl.
G01N 21/00 (2006.01)
G01N 21/956 (2006.01)

(52) U.S. Cl.
CPC ............... G01N 21/95607 (2013.01); G01N 2021/95615 (2013.01); G01N 2021/95676 (2013.01)

(58) Field of Classification Search
CPC .... G01J 3/50; G01J 3/524; G01J 3/504; G01J 3/52; G01J 3/26; G01J 3/02; G01J 3/0202; G01J 3/0205; G01J 3/0237; G01J 3/46; G02B 1/043; G02B 1/105; G02B 5/3083; G02B 1/10; G02B 1/11; G02B 1/12
See application file for complete search history.

(56) References Cited

U.S. PATENT DOCUMENTS

| 2004/0036860 | A1* | 2/2004 | Hiruta | G01N 21/95607 356/237.1 |
| 2009/0191475 | A1* | 7/2009 | Lee | B82Y 10/00 430/5 |
| 2012/0112066 | A1* | 5/2012 | Ogiso | G06T 7/001 250/307 |
| 2014/0312224 | A1* | 10/2014 | Murakawa | H01J 37/28 250/307 |

FOREIGN PATENT DOCUMENTS

| KR | 1020100101828 | 9/2010 |
| KR | 1020120007975 | 1/2012 |

* cited by examiner

Primary Examiner — Michael P Stafira
(74) Attorney, Agent, or Firm — IP & T Group LLP

(57) ABSTRACT

A method of defect inspection for a photomask is provided. According to the method, a light transmittance correction is performed to reduce a light transmittance of a calibration key pattern region of a photomask including a field region and the calibration key pattern region to the light transmittance of the field region. Light calibration is performed using the calibration key pattern region having corrected light transmittance. Defect inspection for the field region is performed by applying a result of the light calibration.

14 Claims, 8 Drawing Sheets

METHODS OF DEFECT INSPECTION FOR PHOTOMASKS

CROSS-REFERENCE TO RELATED APPLICATION

The present application claims priority under 35 U.S.C 119(a) to Korean Application No. 10-2016-0020499, filed on Feb. 22, 2016, which is herein incorporated by reference in its entirety as set forth in full.

BACKGROUND

1. Technical Field

Various embodiments of the present disclosure relate to lithography technologies and, more particularly, to methods of defect inspection for a photomask.

2. Related Art

As semiconductor devices become more highly integrated, a wavelength of light generated from a light source used in photolithography processes has been continuously shorter and shorter to transfer finer patterns onto a wafer. In order to transfer finer patterns, mask patterns which are transferred onto the wafer need to have a small line width or a small line pitch. In case that pattern errors occur, such as overlay errors, after performing the photolithography processes using the photomask, a photomask correction process to correct or to improve such pattern errors may be performed. The photomask correction process may change light transmittance of a field region of the photomask, in which the mask patterns are located, thus inspection noise may be generated during the defect inspection process of the photomask.

SUMMARY

According to one embodiment, there is provided a method of defect inspection for a photomask. The method includes obtaining registration errors existing in a field region of the photomask, wherein the photomask includes the field region and a calibration key pattern region, obtaining a first light transmittance of the field region, performing registration correction by irradiating a first laser beam onto the field region, obtaining a first transmittance reduction in the field region by the registration correction, obtaining a second light transmittance in the field region using the first transmittance reduction, performing light transmittance correction to the calibration key pattern region so that the calibration key pattern region has light transmittance substantially equal to the second light transmittance, performing light calibration using the corrected calibration key pattern region to obtain a light calibration result, and performing defect inspection to the field region by using the light calibration result.

According to one embodiment, there is provided a method of defect inspection for a photomask. The method includes performing registration correction by irradiating a first laser beam onto a field region of the photomask to form a registration corrected field region, wherein the photomask includes the field region and a calibration key pattern region, performing light transmittance correction to reduce light transmittance of the calibration key pattern region, performing light calibration using the reduced light transmittance of the calibration key pattern region to obtain a result of the light calibration, and performing defect inspection to the registration corrected field region by applying the result of the light calibration.

According to one embodiment, there is provided a method of defect inspection for a photomask. The method includes performing light transmittance correction to reduce light transmittance of a calibration key pattern region of the photomask to a corrected light transmittance, wherein the corrected light transmittance is substantially equal to light transmittance of a field region, wherein the photomask includes the field region and the calibration key pattern region; performing light calibration using the calibration key pattern region having the corrected light transmittance to obtain a result of the light calibration, and performing defect inspection to the field region by applying the result of the light calibration.

BRIEF DESCRIPTION OF THE DRAWINGS

Various embodiments of an inventive concept will become more apparent in view of the attached drawings and accompanying detailed description, in which.

DETAILED DESCRIPTION OF THE EMBODIMENTS

Figure 1:
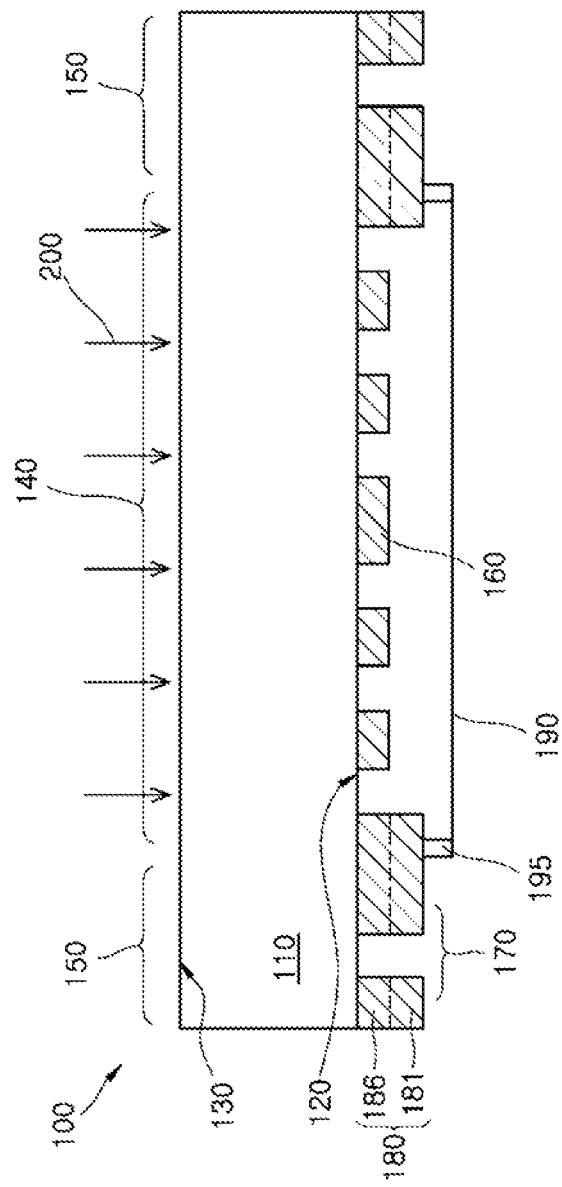
FIGS. 1 to 3 are schematic views illustrating a photomask according to an embodiment.

The terms used herein may correspond to words selected in consideration of their functions in the embodiments, and the meanings of the terms may be construed to be different according to ordinary skill in the art to which the embodiments belong. If defined in detail, the terms may be construed according to the definitions. Unless otherwise defined, the terms used herein have the same meaning as commonly understood by one of ordinary skill in the art to which the embodiments belong.

It will be understood that although terms first, second, third etc. may be used herein to describe various elements, these elements should not be limited by these terms. These terms are only used to distinguish one element from another element. Thus, a first element in some embodiments could be termed a second element in other embodiments without departing from the teachings of the inventive concept.

It will also be understood that when an element or layer is referred to as being "on," "over," "below," "under," or "outside" another element or layer, the element or layer may be in direct contact with the other element or layer, or Intervening elements or layers may be present. Other words used to describe the relationship between elements or layers should be interpreted in a like fashion for example, "between" versus "directly between" or "adjacent" versus "directly adjacent".

The terminology "pattern" used herein may indicate a mask pattern such as a light blocking pattern or a phase shift pattern that is formed on a photomask to realize an element of an electronic circuit or an integrated circuit of a semiconductor device. The semiconductor device may correspond to a memory device or a logic device. The memory device may be a dynamic random access memory (DRAM) device, a static random access memory (SRAM) device, a flash memory device, a magnetic random access memory (MRAM) device, a resistive random access memory (ReRAM) device, a ferroelectric random access memory (FeRAM) device, or a phase change random access memory (PcRAM) device. The semiconductor device may be employed in communication systems such as mobile phones, electronic systems associated with biotechnology or health care, or wearable electronic systems.

Same reference numerals refer to same elements throughout the specification. Thus, even though a reference numeral is not mentioned or described with reference to a drawing, the reference numeral may be mentioned or described with reference to another drawing. In addition, even though a reference numeral is not shown in a drawing, it may be mentioned or described with reference to another drawing.

Figure 2:
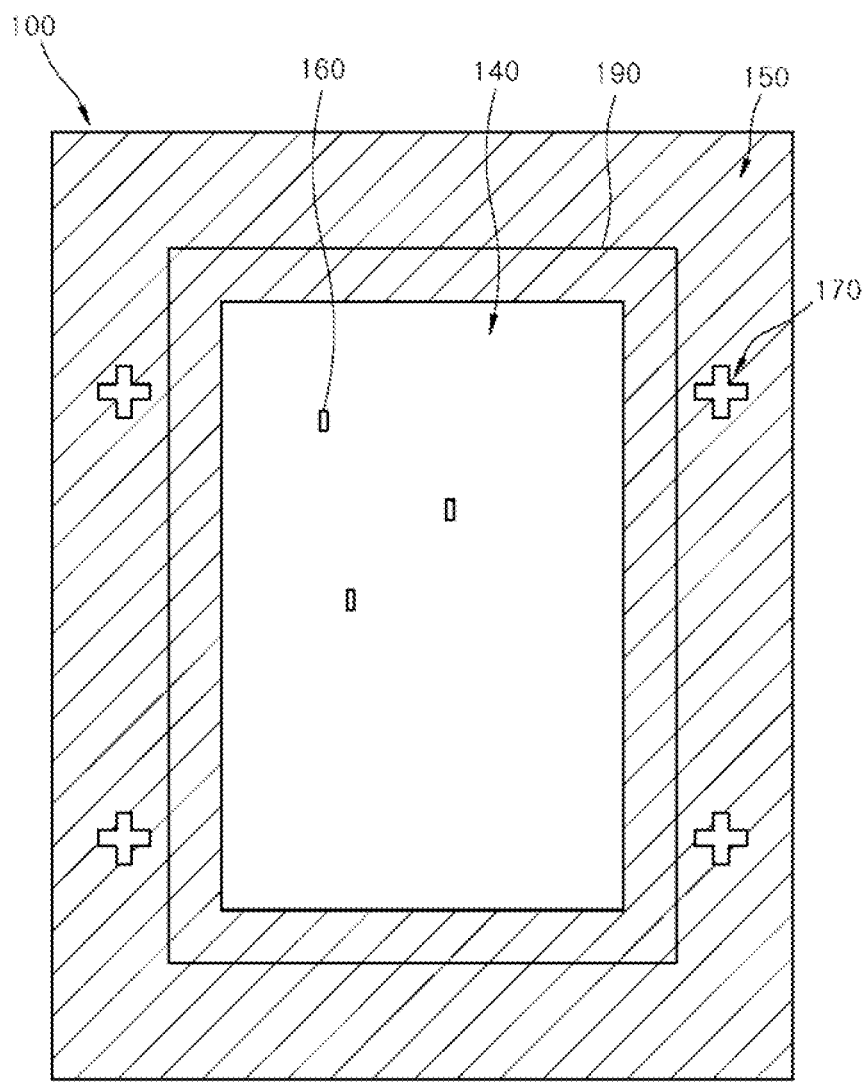
Figure 3:
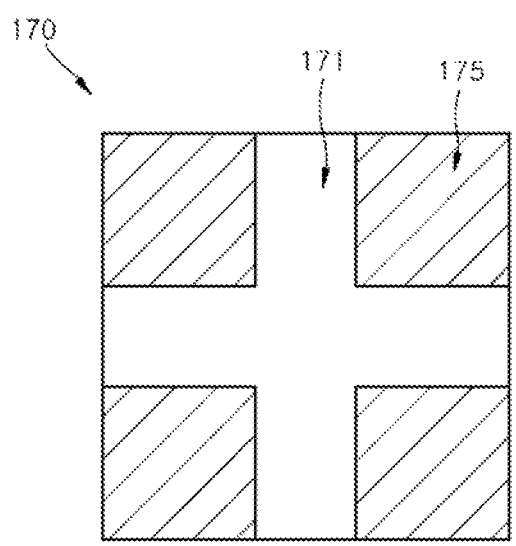

FIG. 1 schematically illustrates a cross-sectional feature of a transmissive photomask 100. FIG. 2 schematically illustrates a planar feature of the photomask 100. FIG. 3 schematically illustrates a planar feature of a calibration key pattern 170.

Referring to FIGS. 1 and 2, a transmissive photomask 100 may be prepared as a photolithography mask used in a photolithography process. The photomask 100 includes a substantially transparent substrate 110. The transparent substrate 110 includes a front side or a first surface 120 and a back side or a second surface 130 opposite to the first surface 120. The substrate 110 may be formed of a transparent material, for example, quartz. The transparent material may be a material capable of transmitting a deep ultra violet (DUV) light, for example, light with approximately a 193 nm wave length band, which may be used as an exposure light 200.

Mask patterns 160 providing features to be transferred onto a wafer may be disposed on the first surface 120 of the photomask 100. The features provided by the mask patterns 160 may be transferred onto the wafer by an exposure process. A region where the mask patterns 160 providing features to be transferred onto the wafer are located is an active region and may be set as a field region 140 located in the photomask 100. An outer region of the field region 140 is an inactive region and may be set as a frame region 150.

The mask pattern 160 may include a layer of a light blocking material such as chrome (Cr), or may include a phase shift layer such as molybdenum silicon (MoSi) layer. The frame region 150 may include a frame layer 180 substantially including a light blocking layer 181, or a double-layer of the light blocking layer 181 and a phase shift layer 186. The exposure light 200 may not pass through the frame region 150, thus the features in the frame region 150 cannot be transferred onto the wafer.

A pellicle 190 to protect the mask patterns 160 may be attached over the field region 140. A pellicle supporting portion 195 supporting the pellicle 190 may be attached on the frame layer 180. The pellicle 190 can prevent the mask patterns 160 from being exposed to an external environment.

After manufacturing the photomask 100, a process of inspecting the photomask 100 is performed to determine whether defects are generated on the photomask 100. For example, during performing an exposure process using the photomask 100, defects known as haze may be generated on the photomask 100, and a process for inspecting the defects may be performed. To improve inspection accuracy of the defect inspection process, sensitivity to detect the defects may be set by performing light calibration, and then, a defect inspection for the field region 140 may be performed. Calibration key patterns 170 for the light calibration may be disposed in an outer region of the field region 140 or in the frame region 150.

A plurality of the calibration key patterns 170 may be disposed in a plurality of locations in the frame region 150 outside the field region 140, as illustrated in FIG. 2. The calibration key pattern 170 may be formed by patterning the frame layer 180 in a predetermined feature.

As illustrated in FIG. 3, each of the calibration key patterns 170 may include a dark pattern 175 and a clear pattern 171. The clear pattern 171 may be defined by the dark pattern 175 and be formed in a cross shape. The dark pattern 175 may be set by a portion of the frame layer 180. The clear pattern 171 may be a quartz portion of the substrate 110, which is exposed by the frame layer 180. The clear pattern 171 may be a substantially transparent feature region.

The clear pattern 171 may be used as a clear level that can be a reference to determine the upper limit of transmittance that can be detected in the defect inspection. The dark pattern 175 may be used as a dark level that can be a reference of light blocked by the light blocking layer 181 forming the frame layer 180, for example, a reference used to determine the lower limit of the transmittance that can be detected in the defect inspection.

By performing light calibration using the calibration key patterns 170, data of a detection light detected by irradiating an inspection light onto the field region 140 of the photomask 100, for example, light transmittance may be calibrated between the clear level and the dark level. The light calibration may be performed to improve the reliability of defect inspection results by adjusting the inspection sensitivity of the photomask 100.

Referring to FIG. 1, the photomask 100 may allow an exposure wavelength of an extreme ultra violet (EUV) wavelength range, for example, approximately 13.5 nm to pass through. The EUV mask structure may include a multi-layered mirror structure for reflection of the EUV.

Referring to FIG. 1 again, wafer patterns such as resist patterns (not illustrated) may be formed by transferring images of the mask patterns 160 on the wafer (not illustrated) using the photomask 100. The formed resist patterns may not exactly correspond to a predetermined structure as originally intended. This type of errors can be referred to as registration errors. Such registration errors may generally be exemplified in a two-dimensional (2D) map 230. See arrows in FIG. 4.

Figure 4:
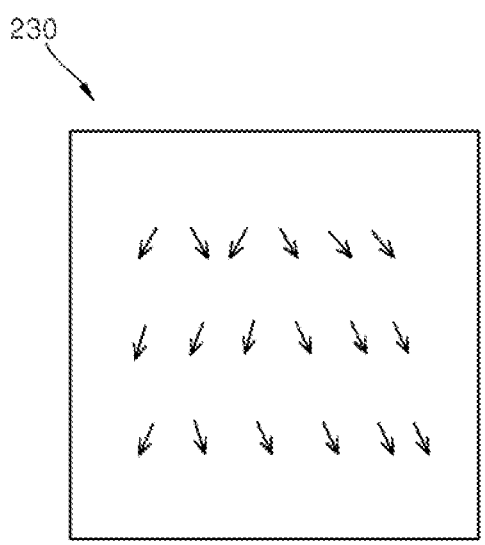
FIG. 4 is a schematic view illustrating a registration error map according to an embodiment.

FIG. 4 illustrates an example of the registration error map 230. The direction of the arrow of the registration error map 230 represents a direction that the pattern components are shifted from an intended pattern location, and the length of the arrow represents the amount of shift. The registration error can be caused by many factors included in the photolithography process, but a registration correction process for the photomask 100 can be carried out to correct the factors due to the photomask 100.

The registration correction process may include a step of measuring the registration errors shown in the registration error map 230 of FIG. 4, and performing a correction process for the photomask 100 using a laser to compensate for the registration errors. The registration correction process using a laser, as illustrated in FIG. 5, may be performed using a registration correction (RegC) system 300.

Figure 5:
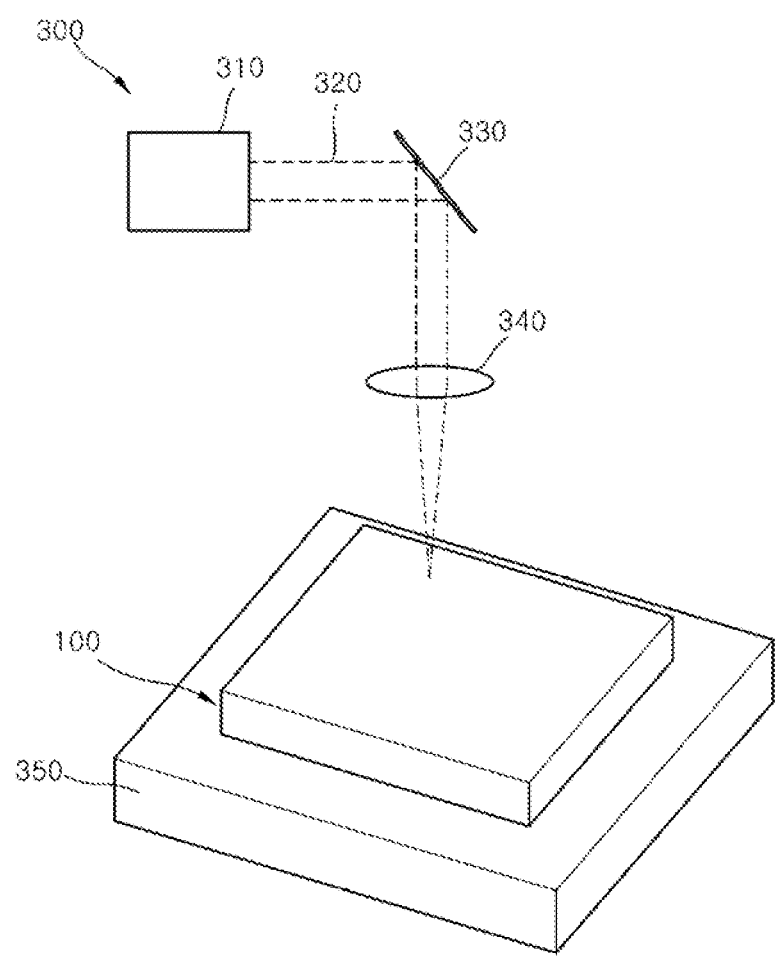
FIG. 5 is a schematic view illustrating a registration correction system according to an embodiment.

Referring to FIG. 5, the registration correction system 300 includes a chuck 350 on which the photomask 100 is seated. In an embodiment, the chuck 350 may be movable in three dimensions. The registration correction system 300 includes a pulsed laser source 310 generating a pulsed beam, an optical pulsed beam or a laser beam 320.

The laser source 310 may generate optical pulses. Although the registration correction system 300 is exemplified to include only one laser source 310 in this embodiment, the registration correction system 300 may include one or more laser sources generating a laser beam of different wavelength bands or the same wavelength band.

A steering mirror 330 and a focus objective lens 340 may be arranged between the laser source 310 and photomask 100. The steering mirror 330 directs the pulse laser beam 320 emitted from the laser source 310 to the focus objective lens 340. The pulse laser beam 320 is focused on the photomask 100 through the focus objective lens 340. In an embodiment, the focus objective lens 340 may be arranged to be movable in three dimensions. The registration correction process may be performed by irradiating a laser beam onto the photomask 100 through the registration correction system 300. As the laser beam is irradiated onto the photomask 100, local errors of the photomask 100 can be corrected.

Figure 6:
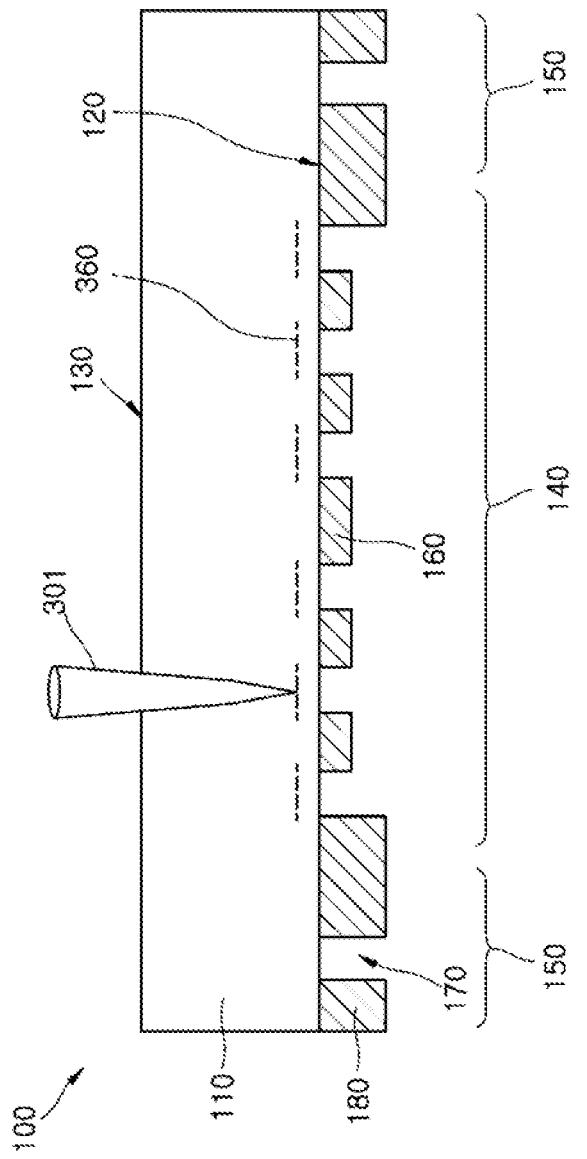
FIG. 6 is a cross-sectional view illustrating a registration correction process according to an embodiment.

FIG. 6 illustrates the registration correction process according to an embodiment. Referring to FIG. 6, a first laser beam 301 for registration correction is irradiated onto the substrate 110 of the photomask 100 using the registration correction system 300 of FIG. 5. A beam spot of the first laser beam 301 may be irradiated to the field region 140 of the substrate 110. The first laser beam 301 may be scanned to the substrate 110 to be irradiated to a plurality of local regions of the substrate 110.

As illustrated in the registration error map 230 of FIG. 4, the errors located in the field region 140 may have different sizes and different directions. To correct the errors illustrated in the registration error map 230 of FIG. 4, the first laser beam 301 may be irradiated with different beam spot densities or different energies to the local regions corresponding to the field region 140 of the substrate 110.

The first laser beam 301 irradiated onto the substrate 110 of the photomask 100 may be incident through the second surface 130 to the substrate 110. The first laser beam 301 may cause first deformation elements 360 in the quartz material constituting the substrate 110. The first deformation element 360 may have a three dimensional volume and may have a morphological organization of atoms. That is, the deformation element 360 is relatively less dense in packing structure or has a lower density than the quartz material therearound. The acting direction or size of the first deformation elements 360 may vary depending on pulse energy, pulse length, a repetition rate, or the number of repeated scans of the first laser beam 301. The registration errors generated differently with respect to the local regions can be corrected by inducing the first deformation elements 360.

The first deformation elements 360 applied to correct the registration errors may change a light transmittance of the field region 140. The light transmittance of the local regions in the field region 140 may be dropped in different amounts depending on density of the first deformation elements 360. This may cause an overall drop of the light transmittance in the field region 140. The overall drop of the light transmittance of the field region 140 may be evaluated as an average value of drops in the light transmittance of the local areas.

The average drop of the light transmittance in the field region 140 of the photomask 100 caused by the registration correction process may cause unexpected difficulties to the defect correction for the photomask 100. The average light transmittance of the field region 140 of the photomask 100 after the registration correction can be relatively decreased compared with the average light transmittance in the field region 140 of the photomask 100 before the registration correction.

Furthermore, the light transmittance of the calibration key pattern region 170 after the registration correction may not be varied or may be relatively slightly varied. Accordingly, the difference between the light transmittance of the calibration key pattern region 170 and the average light transmittance of the field region 140 of the photomask 100 after registration correction can be quite large.

When performing light calibration based on the calibration key pattern region 170 having relatively high light transmittance, defect inspection sensitivity for the field region 140, which has relatively low light transmittance, may increase. Accordingly, an error may occur of misrecognizing a normal pattern as a defect. Erroneous correction to the normal pattern may be cause.

Despite the fact that critical dimension uniformity is not substantially changed by the registration correction, inspection result data containing a large number of defects may be obtained. The detection sensitivity, which is overly high, erroneously determines a non-defect to be a defect. As a result, a noise due to such erroneous detection may increase significantly. For example, sub-resolution assist features (SRAFs) may be detected as a defect that is a noise in the result data. The increase of noise in the defect inspection result data may not only make defect inspection itself erroneous but also acts as a constraint when applying the registration correction process.

Scan of the first laser beam 301 to correct the registration errors may affect the light transmittance or luminance of the calibration key pattern region 170. The first deformation elements 360 caused to the field region 140 by the first laser beam 301 may cause a local and irregular expansion of the photomask 100. Accordingly, the light transmittance or luminance of the calibration key pattern region 170 may vary differently depending on the location of the calibration key patterns 170.

When the calibration key patterns regions 170 have different light transmittances from each other, the accuracy and effectiveness of the light calibration may be degraded. The reliability of the light calibration is degraded and the defect inspection result may include a large number of noises, thus the reliability of the defect inspection may be degraded. The light transmittance difference between the field region 140 subjected to registration correction and calibration key pattern region 170 can be compensated for by reducing the light transmittance of the calibration key pattern region 170.

Figure 7:
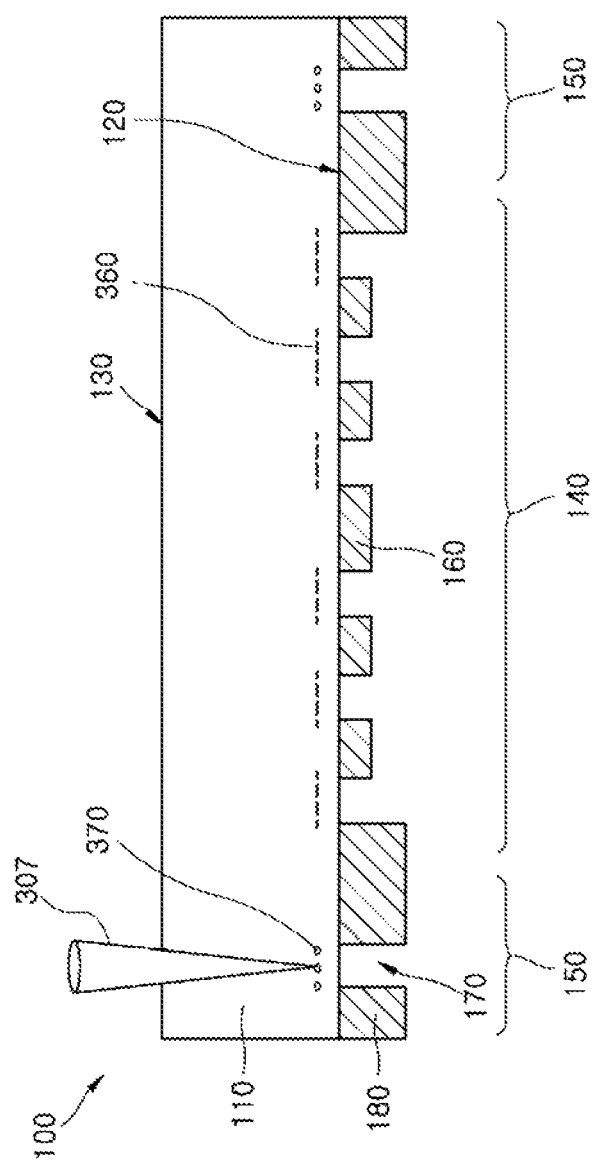
FIG. 7 is a cross-sectional view illustrating a process of reducing light transmittance of a calibration key pattern region of a photomask according to an embodiment.

FIG. 7 illustrates a process of reducing the light transmittance in the calibration region including the calibration key patterns 170 of the photomask 100. Referring to FIG. 7, a second laser beam 307 for reducing light transmittance is irradiated onto the calibration key pattern region 170 of the photomask 100 using the registration correction system 300 of FIG. 5. A beam spot of the second laser beam 307 is irradiated onto the calibration key pattern region 170 and may cause second deformation elements 370. The second deformation elements 370 may have a three dimensional volume and may have a morphological organization of atoms having a relatively less dense packing structure and a lower density than the quartz material therearound.

The light transmittance of the calibration key pattern region 170 may be reduced by the second deformation elements 370. The second deformation elements 370 may reduce the light transmittance of the calibration key pattern region 170 so that the light transmittance of the calibration key pattern region 170 is similar to or substantially equal to the light transmittance of the registration corrected field region 140.

Since a degree of reduction of light transmittance can be varied by the density or size of the second deformation elements 370, desired light transmittance reduction can be obtained by adjusting the energy of the second laser beam 307 or the density of a beam spot of the second laser beam 307 causing the second deformation elements 370.

For example, as illustrated in FIG. 6, the average initial value of a first light transmittance for the field region 140 can be obtained before irradiating the first laser beam 301 of FIG. 6 for registration correction. Then, an amount of the first light transmittance reduction caused by the process of irradiating the first laser beam 301 of FIG. 6 for registration correction to the field region 140 can be obtained from a correlation between the average initial value of the first light transmittance for the field region 140 and the light transmittance reduction after the irradiation of the first laser beam 301.

The average second light transmittance for the field region 140 after the registration correction can be obtained from an amount of the detected first transmittance reduction. After obtaining the initial value of a third light transmittance for the calibration key pattern region 170 prior to the registration correction, a difference between the third light transmittance for the calibration key pattern region 170 before the registration correction and the average second light transmittance for the field region 140 after the registration correction can be obtained as the amount of a second transmittance reduction.

Parameters for the second laser beam 307 to obtain the amount of the second transmittance reduction may be set from the correlation between light transmittances according to irradiation of the second laser beam 307. The second laser beam 307 may be irradiated onto the calibration key pattern region 170 by applying the obtained parameters for irradiation of the second laser beam 307, for example, the type of the second laser beam 307, the energy or density of the beam spot, and so on. Accordingly, the calibration key pattern region 170 may be induced to have a fourth light transmittance that is substantially equal to or similar to the average second light transmittance for the field region 140 after the registration correction.

Since the corrected fourth light transmittance of the calibration key pattern region 170 has a reduced value compared to the third light transmittance, the calibration key pattern region 170 whose light transmittance is corrected may provide a new reference of light calibration. By performing light calibration using the corrected calibration key pattern region 170 having reduced light transmittance, references such as the sensitivity of defect inspection may be reset or updated and defect inspection may be performed for the field region 140 on which the registration correction is performed.

Result data of defect inspection may be calibrated to values between the clear level and dark level which are reset or updated by the light calibration using the calibration key pattern region 170 having the reduced light transmittance after irradiation of the second laser beam 307. Since the light transmittance of the corrected calibration key pattern region 170 is reduced, light calibration using the corrected calibration key pattern region 170 may function to reset the inspection sensitivity for the field region 140 to meet the reduced light transmittance of the field region 140. Accordingly, a noise which is caused by erroneously correcting a non-defective pattern may be avoided.

The light calibration using the corrected calibration key pattern region 170 can eliminate noises and improve the reliability of the defect inspection result by re-adjusting the inspection sensitivity for the photomask 100. By excluding noises, it is possible to overcome a burden for the defect inspection and to overcome the limitations of applying the registration correction process.

The light transmittance correction using the second laser beam 307 may be performed to the calibration key pattern regions 170 which are located in different locations from each other. As a result, the calibration key pattern regions 170 may have substantially the same fourth light transmittance. Accordingly, the phenomenon that the calibration key pattern regions 170 located in different locations from each other have different light transmittances can be compensated for. Since the calibration key pattern regions 170 located in different locations from each other can have substantially the same fourth light transmittance by the light transmittance correction using the second laser beam 307, the reliability of the light calibration process based on the calibration key pattern regions 170 can be improved and the reliability of the defect inspection can be improved.

Figure 8:
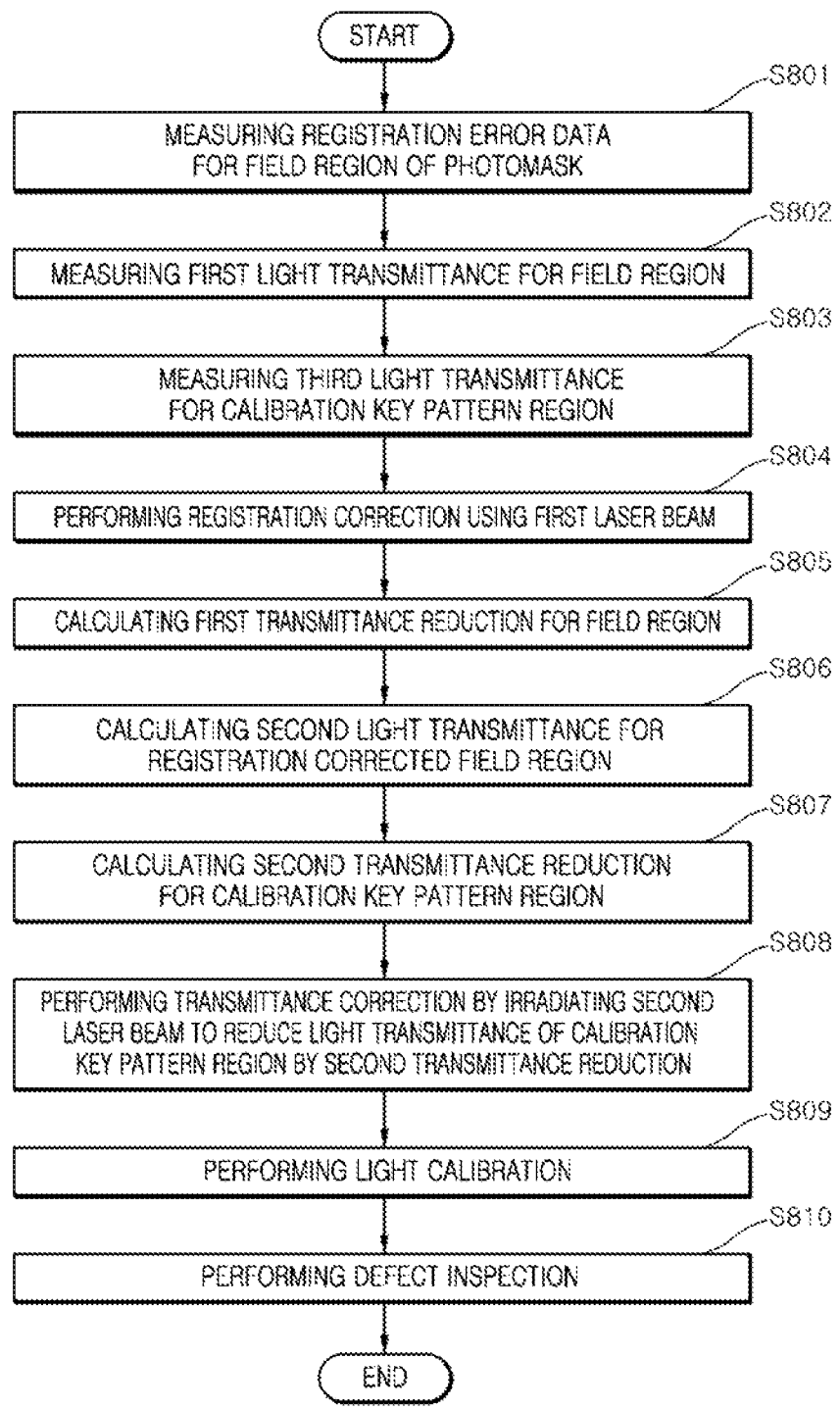
FIG. 8 is a process flow chart illustrating a method of defect inspection of a photomask according to an embodiment.

FIG. 8 is a flow chart illustrating a method of defect inspection for a photomask according to an embodiment. Referring to FIG. 8, defect inspection for the photomask according to an embodiment may be performed by fabricating the photomask 100 as illustrated in FIG. 1, and measuring registration error data for the field region 140 and obtaining the registration error map 230 as illustrated in FIG. 4 (S801). An initial value of the first light transmittance for the field region 140 may be measured (S802). The third light transmittance for the calibration key pattern region 170 may be measured (S803). The registration correction process may be performed by irradiating the first laser beam 301 onto the field region 140 of the photomask 100 of FIG. 1, as illustrated in FIG. 6, using the registration correction system 500 of FIG. 5 illustrated in FIG. 5 (S804).

The first transmittance reduction associated with the registration correction for the field region 140 of FIG. 1 may be calculated (S805). The second light transmittance for the field region 140 of FIG. 1 after the registration correction may be calculated from the first light transmittance and the first transmittance reduction (S806). As illustrated in FIG. 7, the second laser beam 307 may be irradiated onto the calibration key pattern region 170 to reduce a difference between the light transmittance of the calibration key pattern region 170 and the light transmittance of the field region 170 using the second transmittance reduction (S808).

The light calibration may be performed using the corrected light transmittance of the calibration key pattern region 170 (S809). Then, defect inspection for the field region 140 may be performed by applying the light calibration result (S810). Defects detected in the defect inspection may be foreign substances such as haze or particles, which may be attached to or created by the photomask 100 by the exposure light source.

In the method of defect inspection for the photomask, as described with reference to FIG. 6, registration correction may be performed by irradiating the first laser beam 301 onto the field region 140 of the photomask 100 of FIG. 1, and, as illustrated in FIG. 7, the light transmittance correction to reduce the light transmittance of the calibration key pattern region 170 of the photomask 100 may be performed.

In the method of defect inspection for the photomask, as illustrated in FIG. 1, the photomask 100 includes the field region 140 and the calibration key pattern region 170. When a difference between the light transmittances of the field region 140 and the calibration key pattern region 170 is great, the light transmittance correction process may be performed to reduce the light transmittance of the calibration key pattern region 170 to be substantially equal to the light transmittance value of the field region 140, as illustrated in FIG. 7.

The methods according to the aforementioned embodiments and structures formed thereby may be used in photolithography processes for fabricating integrated circuit (IC) chips. The IC chips may be supplied to users in a raw wafer form, in a bare die form or in a package form. The IC chips may also be supplied in a single package form or in a multi-chip package form. The IC chips may be integrated in intermediate products such as mother boards or end products to constitute signal processing devices. The end products may include toys, low end application products, or high end application products such as computers. For example, the end products may include display units, keyboards, or central processing units (CPUs).

The embodiments of the inventive concept have been disclosed above for illustrative purposes. Those of ordinary skill in the art will appreciate that various modifications, additions and substitutions are possible, without departing from the scope and spirit of the inventive concept as disclosed in the accompanying claims.

What is claimed is:

1. A method of defect inspection for a photomask, the method comprising:
   obtaining registration errors existing in a field region of the photomask, wherein the photomask includes the field region and a calibration key pattern region;
   obtaining a first light transmittance of the field region;
   performing registration correction by irradiating a first laser beam onto the field region;
   obtaining a first transmittance reduction in the field region by the registration correction;
   obtaining a second light transmittance in the field region by using the first transmittance reduction;
   performing light transmittance correction to the calibration key pattern region so that the calibration key pattern region has light transmittance substantially equal to the second light transmittance;
   performing light calibration using the corrected calibration key pattern region to obtain a light calibration result; and
   performing defect inspection to the field region by using the light calibration result.

2. The method of claim 1, wherein the first laser beam forms local first deformation elements in the field region to compensate for the registration errors.

3. The method of claim 2, wherein the first deformation elements change the first light transmittance of the field region to the second light transmittance.

4. The method of claim 1, wherein the performing of the light transmittance correction includes forming second deformation elements in the calibration key pattern region.

5. The method of claim 4, wherein the second deformation elements are formed by irradiating a second laser beam onto the calibration key pattern region.

6. The method of claim 4, wherein the performing of the light transmittance correction comprises:

obtaining a third light transmittance of the calibration key pattern region before the light transmittance correction;
   calculating a second transmittance reduction using a difference between the second light transmittance and third light transmittance; and
   irradiating a second laser beam so that the second deformation elements are formed to reduce the third light transmittance of the calibration key pattern region to a fourth transmittance.

7. A method of defect inspection for a photomask, the method comprising:
   performing registration correction by irradiating a first laser beam onto a field region of the photomask to form a registration corrected field region, wherein the photomask includes the field region and a calibration key pattern region;
   performing light transmittance correction to reduce light transmittance of the calibration key pattern region;
   performing light calibration using the reduced light transmittance of the calibration key pattern region to obtain a result of the light calibration; and
   performing defect inspection to the registration corrected field region by applying the result of the light calibration.

8. The method of claim 7, wherein the first laser beam forms local deformation elements to the photomask.

9. The method of claim 8, wherein the first deformation elements reduce light transmittance of the field region.

10. The method of claim 7, wherein the performing of the light transmittance correction includes forming second deformation elements in the calibration key pattern region.

11. The method of claim 10, wherein the second deformation elements are formed by irradiating a second laser beam onto the calibration key pattern region to make the reduced light transmittance of the calibration key pattern region substantially equal to light transmittance of the registration corrected field region.

12. A method of defect inspection for a photomask, the method comprising:
    performing light transmittance correction to reduce light transmittance of a calibration key pattern region of the photomask to a corrected light transmittance, wherein the corrected light transmittance is substantially equal to light transmittance of a field region, wherein the photomask includes the field region and the calibration key pattern region; performing light calibration using the calibration key pattern region having the corrected light transmittance to obtain a result of the light calibration; and
    performing defect inspection to the field region by applying the result of the light calibration.

13. The method of claim 12, wherein the performing of the light transmittance correction includes forming deformation elements in the calibration key pattern region.

14. The method of claim 13, wherein the deformation elements are formed by irradiating a laser beam onto the calibration key pattern region.

* * * * *